(12) United States Patent
Nobis et al.

(10) Patent No.: US 7,837,620 B2
(45) Date of Patent: Nov. 23, 2010

(54) MEDICAL TUBULAR ASSEMBLY

(75) Inventors: Rudolph H. Nobis, Mason, OH (US); Ifung Lu, Skokie, IL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1247 days.

(21) Appl. No.: 11/411,195

(22) Filed: Apr. 25, 2006

(65) Prior Publication Data

US 2007/0249905 A1  Oct. 25, 2007

(51) Int. Cl.
*A61B 1/00* (2006.01)

(52) U.S. Cl. .......................... 600/142; 606/1; 600/139; 600/141

(58) Field of Classification Search .................. 600/142
See application file for complete search history.

(56) References Cited

U.S. PATENT DOCUMENTS

| | | |
|---|---|---|
| 3,470,876 A | 10/1969 | Barchilon |
| 3,521,620 A | 7/1970 | Cook |
| 3,791,387 A | 2/1974 | Itoh |
| 3,799,151 A | 3/1974 | Fakaumi et al. |
| 3,805,791 A | 4/1974 | Seuberth et al. |
| 4,326,530 A | 4/1982 | Fleury, Jr. |
| 4,493,320 A | 1/1985 | Treat |
| 4,638,802 A | 1/1987 | Okada |
| 4,735,194 A | 4/1988 | Stiegmann |
| 4,890,602 A | 1/1990 | Hake |
| 4,893,613 A | 1/1990 | Hake |
| 4,963,147 A | 10/1990 | Agee et al. |
| 5,002,041 A | 3/1991 | Chikama |
| 5,035,696 A | 7/1991 | Rydell |
| 5,066,295 A | 11/1991 | Kozak et al. |
| 5,078,716 A | 1/1992 | Doll |
| 5,171,314 A | 12/1992 | Dulebohn |
| 5,201,732 A | 4/1993 | Parins et al. |
| 5,201,741 A | 4/1993 | Dulebohn |
| 5,250,060 A | 10/1993 | Carbo et al. |
| 5,293,869 A | 3/1994 | Edwards et al. |

(Continued)

FOREIGN PATENT DOCUMENTS

| | | |
|---|---|---|
| DE | 4408730 | 9/1995 |
| DE | 19729499 | 1/1999 |
| EP | 0027704 | 4/1981 |
| EP | 0397489 | 11/1990 |
| EP | 1310206 | 5/2003 |

(Continued)

OTHER PUBLICATIONS

Examination Report, European Application No. 07251728.7 (Dec. 17, 2008).

(Continued)

*Primary Examiner*—Henry M Johnson, III
*Assistant Examiner*—Lynsey Crandall
(74) *Attorney, Agent, or Firm*—Victor C. Moreno

(57) ABSTRACT

A medical tubular assembly includes four medical coilpipes together having a distal end portion insertable into a patient. The four medical coilpipes include a central coilpipe and three peripheral coilpipes disposed outward of the central coilpipe. The four medical coilpipes are wound from a continuous length of wire. In one example, a lengthwise translatable medical-end-effector activation cable is located in the central coilpipe, a separate and lengthwise translatable medical-instrument-member articulation cable is located in each of the three peripheral coilpipes, and the distal end portion is endoscopically insertable into the patient. Other examples are left to those skilled in the art.

18 Claims, 4 Drawing Sheets

U.S. PATENT DOCUMENTS

| | | | |
|---|---|---|---|
| 5,322,505 A | 6/1994 | Krause et al. |
| 5,342,299 A | 8/1994 | Snoke et al. |
| 5,346,504 A | 9/1994 | Ortiz et al. |
| 5,353,807 A | 10/1994 | DeMarco |
| 5,397,304 A | 3/1995 | Truckai |
| 5,409,453 A | 4/1995 | Lundquist et al. |
| 5,431,671 A | 7/1995 | Nallakrishnan |
| 5,433,721 A | 7/1995 | Hooven et al. |
| 5,441,499 A | 8/1995 | Fritzch |
| 5,482,029 A | 1/1996 | Sekiguchi et al. |
| 5,522,829 A | 6/1996 | Michalos |
| 5,531,664 A | 7/1996 | Adachi et al. |
| 5,531,686 A | 7/1996 | Lundquist et al. |
| 5,542,948 A | 8/1996 | Weaver et al. |
| 5,618,294 A | 4/1997 | Aust et al. |
| 5,706,827 A | 1/1998 | Ehr et al. |
| 5,749,828 A | 5/1998 | Solomon et al. |
| 5,752,961 A | 5/1998 | Hill |
| 5,776,080 A | 7/1998 | Thome et al. |
| 5,792,165 A | 8/1998 | Kileman et al. |
| 5,810,715 A | 9/1998 | Moriyama |
| 5,810,807 A | 9/1998 | Ganz et al. |
| 5,836,947 A | 11/1998 | Fleischman |
| 5,848,986 A | 12/1998 | Lundquist et al. |
| 5,865,724 A | 2/1999 | Palmer et al. |
| 5,897,554 A | 4/1999 | Chia et al. |
| 5,972,012 A | 10/1999 | Ream et al. |
| 6,066,102 A | 5/2000 | Townsend et al. |
| 6,071,277 A | 6/2000 | Farley et al. |
| 6,074,408 A | 6/2000 | Freeman |
| 6,093,185 A | 7/2000 | Ellis et al. |
| 6,152,918 A | 11/2000 | Padilla et al. |
| 6,174,280 B1 | 1/2001 | Oneda et al. |
| 6,203,494 B1 | 3/2001 | Moriyama |
| 6,352,503 B1 | 3/2002 | Matsui et al. |
| 6,371,907 B1 | 4/2002 | Hasegawa et al. |
| 6,395,001 B1 | 5/2002 | Ellman et al. |
| 6,423,059 B1 | 7/2002 | Hanson et al. |
| 6,443,943 B1 | 9/2002 | Ouchi |
| 6,443,944 B1 | 9/2002 | Doshi et al. |
| 6,450,948 B1 | 9/2002 | Matsuura et al. |
| 6,451,014 B1 | 9/2002 | Wakikaido et al. |
| 6,454,703 B1 | 9/2002 | Ide |
| 6,454,758 B1 | 9/2002 | Thompson |
| 6,475,222 B1 | 11/2002 | Berg et al. |
| 6,482,149 B1 | 11/2002 | Torii |
| 6,488,658 B1 | 12/2002 | Long |
| 6,500,189 B1 | 12/2002 | Lang et al. |
| 6,569,105 B1 | 5/2003 | Kortenbach et al. |
| 6,579,300 B2 | 6/2003 | Griego et al. |
| 6,602,267 B2 | 8/2003 | Castaneda |
| 6,612,992 B1 | 9/2003 | Hossack et al. |
| 6,663,625 B1 | 12/2003 | Ormsby et al. |
| 6,709,388 B1 | 3/2004 | Mosse et al. |
| 6,730,097 B2 | 5/2004 | Dennis |
| 6,743,240 B2 | 6/2004 | Smith et al. |
| 6,764,441 B2 | 7/2004 | Chiel et al. |
| 6,866,626 B2 | 3/2005 | Long et al. |
| 7,060,024 B2 | 6/2006 | Long et al. |
| 7,060,025 B2 | 6/2006 | Long et al. |
| 7,066,879 B2 | 6/2006 | Fowler et al. |
| 7,093,518 B2 | 8/2006 | Gmeilbauer |
| 7,118,587 B2 | 10/2006 | Dycus et al. |
| 2001/0029397 A1* | 10/2001 | Thompson ............... 623/1.16 |
| 2001/0037084 A1 | 11/2001 | Nardeo |
| 2002/0017515 A1 | 2/2002 | Obata et al. |
| 2002/0087208 A1 | 7/2002 | Koblish et al. |
| 2002/0095168 A1 | 7/2002 | Griego et al. |
| 2002/0120178 A1 | 8/2002 | Tartaglia et al. |
| 2002/0147445 A1 | 10/2002 | Farley et al. |
| 2002/0177802 A1 | 11/2002 | Moutafis et al. |
| 2003/0014051 A1 | 1/2003 | Woloszko |
| 2003/0045778 A1 | 3/2003 | Ohline et al. |
| 2003/0074014 A1 | 4/2003 | Castaneda |
| 2003/0109898 A1 | 6/2003 | Schwartz et al. |
| 2003/0125788 A1 | 7/2003 | Long |
| 2003/0153866 A1 | 8/2003 | Long et al. |
| 2003/0181785 A1 | 9/2003 | Viebach et al. |
| 2003/0195492 A1 | 10/2003 | Gobron et al. |
| 2003/0208219 A1 | 11/2003 | Aznoian et al. |
| 2004/0034343 A1 | 2/2004 | Gillespie et al. |
| 2004/0044350 A1 | 3/2004 | Martin et al. |
| 2004/0068291 A1 | 4/2004 | Suzuki |
| 2004/0092953 A1 | 5/2004 | Salameh et al. |
| 2004/0097919 A1 | 5/2004 | Wellman et al. |
| 2004/0143159 A1 | 7/2004 | Wendlandt |
| 2004/0143160 A1 | 7/2004 | Couvillon, Jr. |
| 2004/0193016 A1 | 9/2004 | Root et al. |
| 2004/0230096 A1 | 11/2004 | Stefanchik et al. |
| 2005/0043743 A1 | 2/2005 | Dennis |
| 2005/0183733 A1 | 8/2005 | Kawano et al. |
| 2005/0203610 A1* | 9/2005 | Tzeng ............... 623/1.22 |
| 2005/0222587 A1 | 10/2005 | Jinno et al. |
| 2005/0234296 A1 | 10/2005 | Saadat et al. |
| 2005/0272975 A1 | 12/2005 | McWeeney et al. |
| 2005/0273084 A1 | 12/2005 | Hinman et al. |
| 2005/0273085 A1 | 12/2005 | Hinman et al. |
| 2006/0009711 A1 | 1/2006 | Gingrich et al. |
| 2006/0089627 A1 | 4/2006 | Burnett et al. |
| 2007/0225562 A1 | 9/2007 | Spivey et al. |

FOREIGN PATENT DOCUMENTS

| | | |
|---|---|---|
| EP | 1849421 | 10/2007 |
| JP | 59-181124 | 10/1984 |
| JP | 2004-154164 | 6/2004 |
| WO | WO 96/00030 | 1/1996 |
| WO | WO 97/12557 | 4/1997 |
| WO | 97/35135 | 9/1997 |
| WO | 99/12489 | 3/1999 |
| WO | 01/08737 | 2/2001 |
| WO | 01/82814 | 11/2001 |
| WO | 01/93938 | 12/2001 |
| WO | 02/43797 | 6/2002 |
| WO | 03/053225 | 7/2003 |
| WO | 03/092476 | 11/2003 |
| WO | 2005/113051 | 12/2005 |
| WO | 2006/019291 | 2/2006 |
| WO | 2006/026687 | 3/2006 |
| WO | 2006/122279 | 11/2006 |

OTHER PUBLICATIONS

European Search Report, European Application No. 07251934 (2 pages) (dated Aug. 30, 2007).

Ginsberg, G.G., "Colonoscopy with the variable stiffness colonoscope," Gastrointestinal Endoscopy, vol. 58, No. 4 (2003).

Brooker, J.C. et al., "A new variable stiffness colonoscope makes colonoscopy easier: a randomised controlled trial," Gut 2000, 46, pp. 801-805 (2000).

Rex, D.K., "Effect of Variable Stiffness Colonoscopes on Cecal Intubation Times for Routine Colonoscopy by an Experienced Examiner in Sedated Patients," EndoscopY; 33 (1), pp. 60-64 (2001).

Shah, S.G., et al., "Magnetic imaging of colonoscopy: an audit of looping, accuracy and ancillary maneuvers," Gastrointestinal Endoscopy, vol. 52, No. 1, pp. 1-8 (2000).

Shah, S.G., et al., "The variable stiffness colonoscope: assessment of efficacy by magnetic endoscope imaging," Gastrointestinal Endoscopy, vol. 56, No. 2, pp. 195-201 (2002).

"Sensors-Resistance," Smart Engineering Group (1999).

* cited by examiner

MEDICAL TUBULAR ASSEMBLY

FIELD OF THE INVENTION

The present invention is related generally to medical equipment, and more particularly to a medical tubular assembly.

BACKGROUND OF THE INVENTION

Medical tubular assemblies are known including an insertion tube of a flexible endoscope (such as a colonoscope). The distal end portion of the polymeric insertion tube is endoscopically insertable within a patient. The insertion tube has an articulatable distal end portion controlled by wires running from the distal end portion to control knobs on the handle of the endoscope. A wide angle video camera in the distal end of the insertion tube permits medical observation. Medical devices, such as a medical snare or a medical grasper, are part of an endoscopic system and are insertable into the working channel(s) of the insertion tube of the endoscope and are translatable to extend from the distal end portion for medical treatment.

Superelastic components, such as a superelastic wire, are known.

Still, scientists and engineers continue to seek improved medical tubular assemblies.

SUMMARY OF THE INVENTION

A first expression of an embodiment of the invention is for a medical tubular assembly including four medical coilpipes together having a distal end portion insertable into a patient. The four medical coilpipes include a central coilpipe and three peripheral coilpipes disposed outward of the central coilpipe. The four medical coilpipes are wound from a continuous length of wire.

A second expression of an embodiment of the invention is for a medical tubular assembly including four medical coilpipes together having a distal end portion insertable into a patient. The four medical coilpipes include a central coilpipe and three peripheral coilpipes disposed outward of the central coilpipe. The four medical coilpipes are wound from a continuous length of superelastic wire.

A third expression of an embodiment of the invention is for a medical tubular assembly including four medical coilpipes together having a distal end portion insertable within a patient. The four medical coilpipes include a central coilpipe and first, second, and third peripheral coilpipes disposed outward of the central coilpipe. The four medical coilpipes consist essentially of a continuous length of wire. One traveling along the wire would make a first loop once around a centerline of the first peripheral coilpipe, then would make a second loop once around a centerline of the second peripheral coilpipe, and then would make a third loop once around a centerline of the third peripheral coilpipe, wherein portions of the traveled wire not including the first, second and third loops would at least partially bound a centerline of the central coilpipe.

Several benefits and advantages are obtained from one or more or all of the expressions of an embodiment of the invention. In a first example, the medical coilpipe assembly has greater bendability compared to a four lumen polymeric insertion tube of a flexible endoscope.

The present invention has, without limitation, application in hand-activated instruments as well as in robotic-assisted instruments.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiment of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described expressions of an embodiment, examples, etc. can be combined with any one or more of the other following-described expressions of an embodiment, examples, etc.

Figure 1:
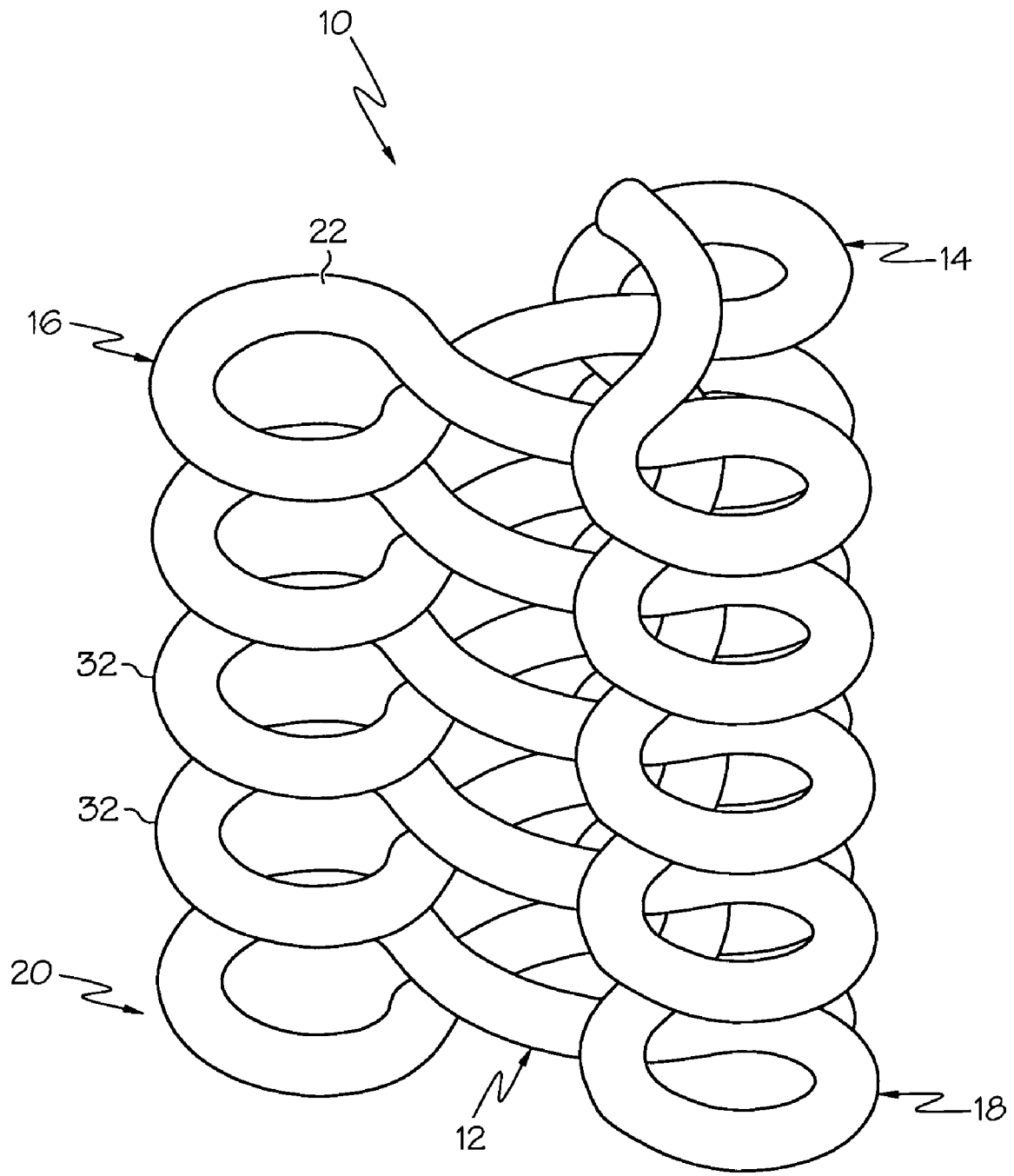
FIG. 1 is a perspective view of a embodiment of the medical tubular assembly of the invention.
Figure 2:
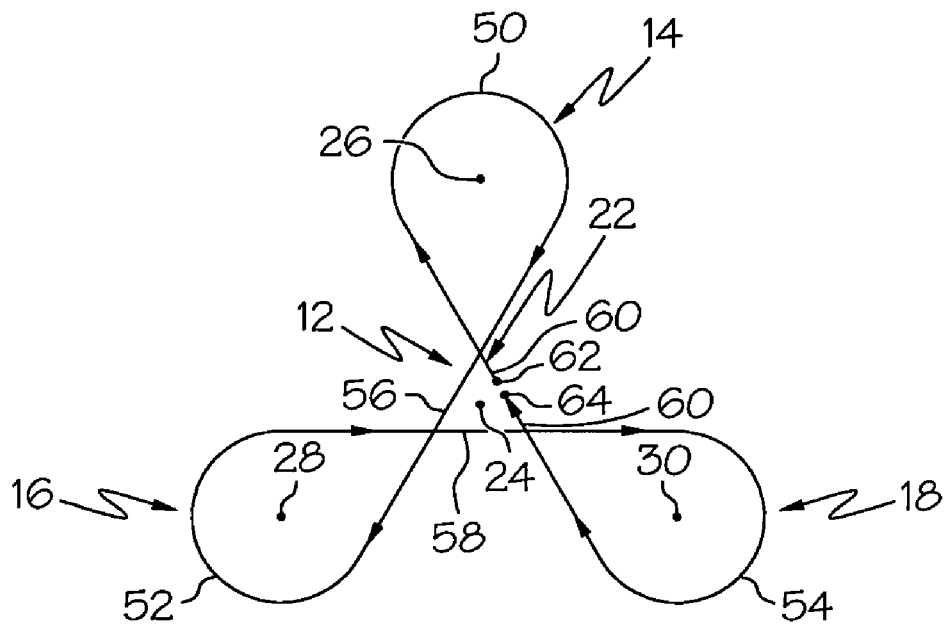
FIG. 2 is a top elevational view of an explanatory diagram showing the beginning of the winding of the wire into the medical tubular assembly of FIG. 1.
Figure 3:
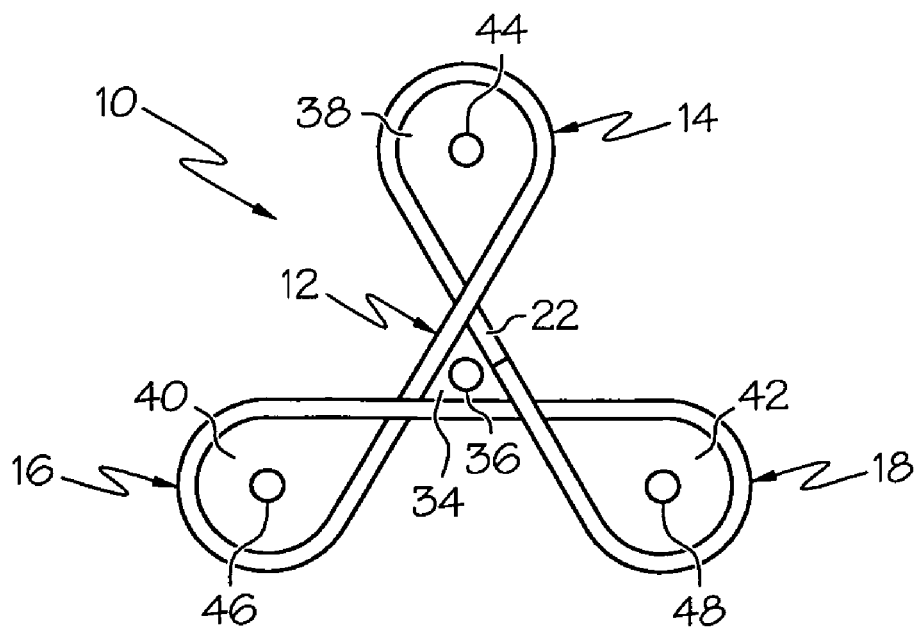
FIG. 3 is a top elevational view of the medical tubular assembly of FIG. 1 with the addition of a medical-end-effector activation cable in the lumen of the central coilpipe and with the addition of a medical-instrument-member articulation cable in the lumen of each of the peripheral coilpipes.

Referring now to the Figures, FIGS. 1-3 illustrate an embodiment of the invention. A first expression of the embodiment of FIGS. 1-3 is for a medical tubular assembly 10 including four medical coilpipes 12, 14, 16 and 18 together having a distal end portion 20 insertable into a patient. The four medical coilpipes 12, 14, 16 and 18 include a central coilpipe 12 and three peripheral coilpipes 14, 16 and 18 disposed outward of the central coilpipe 12. The four medical coilpipes 12, 14, 16 and 18 are wound from a continuous length of wire 22.

It is noted that the term "wire" includes any elongated member adapted for winding into the four medical coilpipes 12, 14, 16 and 18. In one example, without limitation, the wire comprises, consists essentially of, or consists of nitinol. It is also noted that each of the four medical coilpipes 12, 14, 16 and 18 is not limited to a circular structure when viewed on end (as in FIGS. 2-3). In one example, the central coilpipe 12 has a substantially triangular shape when viewed on end (as seen in FIGS. 2-3), and each of the three peripheral coilpipes 14, 16 and 18 has a teardrop shape when viewed on end (as seen in FIGS. 2-3). Other examples of coilpipe shapes when viewed on end are left to the artisan.

In one implementation of the first expression of the embodiment of FIGS. 1-3, the four medical coilpipes 12, 14, 16 and 18 consist essentially of the continuous length of wire 22. In one variation, the four medical coilpipes 12, 14, 16 and 18 consist of the continuous length of wire 22.

In a first example of the first expression of the embodiment of FIGS. 1-3, the wire is a braided wire. In a second example, the wire 22 is a monolithic wire. In a third example, the wire includes two (or more) wire segments with adjacent segments lengthwise joined together (i.e., one end of one segment is joined to one end of another segment). Other examples of a continuous length of wire are left to the artisan. For comparison, an example of four medical coilpipes wound from non-continuous lengths of wire include a first peripheral coilpipe wound from a first continuous length of wire, a second peripheral coilpipe wound from a second continuous length of wire, a third peripheral coilpipe wound from a third continuous length of wire, and a central coilpipe wound from a fourth continuous length of wire, wherein none of the four lengths of wire are lengthwise joined to any other of the four lengths of wire.

In one construction of the first expression of the embodiment of FIGS. 1-3, the four medical coilpipes 12-18 are flexible. In one configuration, each of the central and three peripheral coilpipes 12, 14, 16 and 18 has a centerline 24, 26, 28 and 30 (seen on end as a point in FIG. 2) and wherein the centerlines 26, 28 and 30 of the three peripheral coilpipes 14, 16 and 18 are disposed substantially 120 degrees apart from each other about the centerline 24 of the central coilpipe 12. In one variation, the centerlines 26, 28 and 30 of the three peripheral coilpipes 14, 16 and 18 are disposed a substantially equal distance apart from each other.

In one arrangement of the first expression of the embodiment of FIGS. 1-3, the central and three peripheral coilpipes 12, 14, 16 and 18 each have coil turns 32, and longitudinally adjacent coil turns 32 of each of the central and three peripheral coilpipes 12, 14, 16 and 18 are spaced apart from each other (as seen in FIG. 1).

In one application of the first expression of the embodiment of FIGS. 1-3, the central coilpipe 12 surrounds a central lumen 34, and the medical tubular assembly 10 also includes a lengthwise translatable medical-end-effector activation cable 36 disposed in the central lumen 34. In one variation, the three peripheral coilpipes 14, 16 and 18 each surround a separate peripheral lumen 38, 40 and 42, and the medical tubular assembly 10 also includes a separate and lengthwise translatable medical-instrument-member articulation cable 44, 46 or 48 disposed in each of the separate peripheral lumens 38, 40 and 42. It is noted that the activation cable 36 and the articulation cables 44, 46 and 48 are seen on end in FIG. 3. The term "cable" includes any flexible elongated member.

In one choice of materials, the wire 22 consists essentially of stainless steel. In another choice of materials, the wire 22 consists essentially of a superelastic wire such as nitinol.

A second expression of the embodiment of FIGS. 1-3 is identical to the previously-described first expression of the embodiment of FIGS. 1-3 except that the wire 22 of the first expression is limited to a superelastic wire in the second expression. It is noted that the implementations, examples, constructions, etc. of the first expression of the embodiment of FIGS. 1-3 is equally applicable to the second expression of the embodiment of FIGS. 1-3.

A third expression of the embodiment of FIGS. 1-3 is for a medical tubular assembly 10 including four medical coilpipes 12, 14, 16 and 18 together having a distal end portion 20 insertable within a patient. The four medical coilpipes 12, 14, 16 and 18 include a central coilpipe 12 and first, second, and third peripheral coilpipes 14, 16 and 18 disposed outward of the central coilpipe 12. The four medical coilpipes 12, 14, 16 and 18 consist essentially of a continuous length of wire 22. As seen from FIG. 2, one traveling along the wire 22 would make a first loop 50 once around a centerline 26 of the first peripheral coilpipe 14, then would make a second loop 52 once around a centerline 28 of the second peripheral coilpipe 16, and then would make a third loop 54 once around a centerline 30 of the third peripheral coilpipe 18, wherein portions 56, 58 and 60 of the traveled wire not including the first, second and third loops 50, 52 and 54 would at least partially bound a centerline 24 of the central coilpipe 12.

It is noted that the constructions, arrangements, applications, etc. of the first expression of the embodiment of FIGS. 1-3 are equally applicable to the third expression of the embodiment of FIGS. 1-3.

In one method of any one or more or all of the expressions of the embodiment of FIGS. 1-3, the wire 22 is wound, as seen in FIG. 2, from a starting point 62 in the direction of the arrows to a point 64. Thereafter, the wire 22 is wound (not shown in FIG. 2 but seen in FIG. 1) to repeatedly trace over and above the path shown in FIG. 2 to create the four coilpipes 12, 14, 16 and 18 as seen in FIG. 1. In one example, a mandrel (not shown) is disposed at the location of each lumen 34, 38, 40 and 42 to assist in winding the wire 22 into the shape of the medical tubular assembly 10. Depending on the size of the lumens and the thickness of the wire, a computer numerical control (CNC) coil winding machine should be able to be employed to wind the wire 22 into the shape of the medical tubular assembly 10 without the assistance of mandrels.

In one arrangement of any one or more or all of the expressions of the embodiment of FIGS. 1-3, the medical tubular assembly 10 comprises exactly four medical coilpipes 12, 14, 16 and 18. In one extension, not shown, the medical tubular assembly comprises exactly five medical coilpipes including a central substantially rectangular or square coilpipe and four peripheral coilpipes appearing as loops at the corners of the rectangle or square. Extensions to six or more medical coilpipes including a central polygon coilpipe and peripheral coilpipes appearing as loops at the corners of the polygon are left to those skilled in the art.

Figure 4:
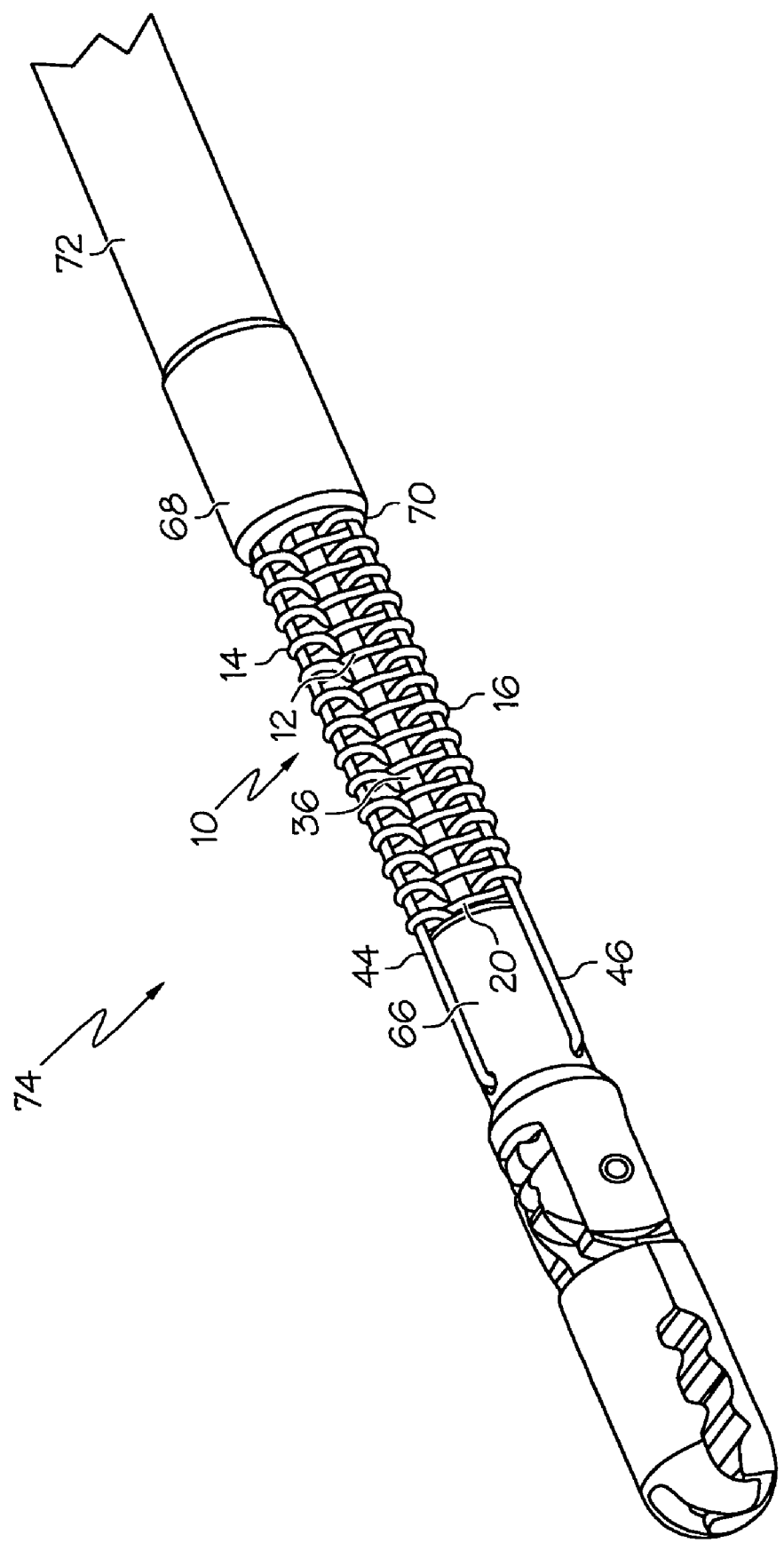
FIG. 4 is a perspective view of the medical tubular assembly of FIG. 1 wherein the medical tubular assembly is shown attached to a distal medical instrument member which is a medical end effector which is a medical grasper.

In one deployment, as shown in FIG. 4, of any one or more or all of the expressions of the embodiment of FIGS. 1-3, the medical tubular assembly 10 (such as the distal end portion 20 thereof) is connected to a distal medical instrument member 66. The example of the distal medical instrument member 66 shown in FIG. 4 is a medical end effector in the form of a medical grasper. Other types of medical end effectors are left to the artisan. In one variation, the medical tubular assembly 10 (such as a proximal end portion 70 thereof) is connected to a proximal medical instrument member 68. In the example of FIG. 4, the proximal medical instrument member 68 is a fitting in the form of an end cap attached to a flexible tube 72 having separate lumens (not shown) for each of the activation and articulation cables. In another example, not shown, the proximal medical instrument member is an end portion of the tube 72. The distal medical instrument member 66 is disposed distal of the proximal medical instrument member 68. FIG. 4 shows the central coilpipe 12 surrounding the activation cable 36, the first peripheral coilpipe 14 surrounding articulation cable 44, and the second peripheral coilpipe 16 surrounding articulation cable 46. In the portion of the medical instrument 74 shown in FIG. 4, the activation cable would be attached to the jaw opening and closing mechanism of the medical grasper. The articulation cables 44 and 46 are shown attached to the medical grasper to articulate the distal medical instrument member 66 (in this example a medical grasper) with respect to the proximal medical instrument member 68. In one option, not shown, the medical tubular assembly 10 is surrounded by a flexible sheath.

Figure 5:
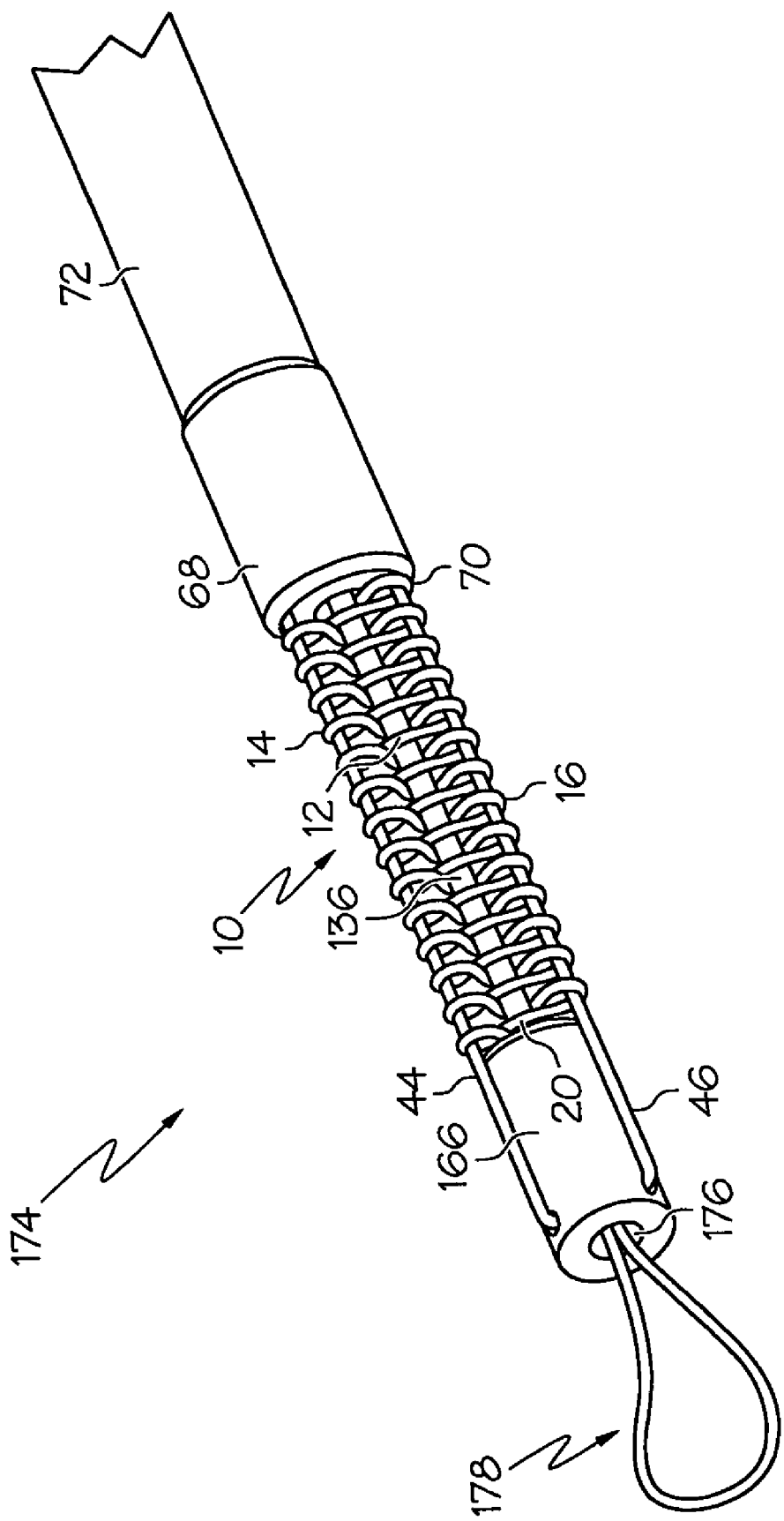
FIG. 5 is a perspective view of the medical tubular assembly of FIG. 1 wherein the medical tubular assembly is shown attached to a distal medical instrument member which is a medical end effector which is a medical snare.

In another deployment, as shown in FIG. 5, of any one or more or all of the expressions of the embodiment of FIGS. 1-3, the medical tubular assembly 10 (such as the distal end portion 20 thereof) is connected to a distal medical instrument member 166. The example of the distal medical instrument member 166 shown in FIG. 4 is a coupling from a lumen 176 of which a medical end effector 178 is extended for medical treatment by moving the activation cable 136. An example of the medical end effector 178 is a medical snare. Other examples are left to the artisan. The medical instrument 174 of FIG. 5 is otherwise identical to the medical instrument 74 of FIG. 4. Other deployments of the medical tubular assembly 10 are left to those skilled in the art.

In one illustration, not shown, of any one or more or all of the expressions of the embodiment of FIGS. 1-3, the medical tube assembly 10 is inserted into a working channel of a flexible insertion tube of an endoscope, wherein the medical end effector can be articulated with respect to the insertion tube of the endoscope allowing independent alignment of the wide angle video camera of the endoscope and the medical end effector. In a second illustration, not shown, the medical tube assembly 10 has a tube-to-endoscope-rail coupling feature allowing the medical tube assembly to be coupled to, and slid along, an exterior rail of a flexible insertion tube of an endoscope allowing independent alignment of the wide angle video camera of the endoscope and the medical end effector. Other illustrations are left to those skilled in the art.

Several benefits and advantages are obtained from one or more or all of the expressions of an embodiment of the invention. In a first example, the medical coilpipe assembly has greater bendability compared to a four lumen polymeric insertion tube of a flexible endoscope.

While the present invention has been illustrated by a description of several expressions of an embodiment, it is not the intention of the applicants to restrict or limit the spirit and scope of the appended claims to such detail. Numerous other variations, changes, and substitutions will occur to those skilled in the art without departing from the scope of the invention. For instance, the medical instrument of the invention has application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. A medical instrument assembly comprising:
    a medical tubular assembly with four medical coilpipes together having a distal end portion insertable within a patient, wherein the four medical coilpipes include a central coilpipe and three peripheral coilpipes disposed outward of the central coilpipe, wherein the four medical coilpipes are wound from a continuous length of wire, and wherein the three peripheral coilpipes each surround a separate peripheral lumen;
    a proximal medical instrument member connected to the medical tubular assembly;
    a distal medical instrument member connected to the distal end portion; and
    a separate and lengthwise translatable medical-instrument-member articulation cable disposed in each of the separate peripheral lumens, wherein the medical-instrument-member articulation cables are attached to the distal medical instrument member to articulate the distal medical instrument member with respect to the proximal medical instrument member.

2. The medical instrument assembly of claim 1, wherein the four medical coilpipes are flexible.

3. The medical instrument assembly of claim 2, wherein each of the central and three peripheral coilpipes has a centerline, and wherein the centerlines of the three peripheral coil pipes are disposed substantially 120 degrees apart from each other about the centerline of the central coilpipe.

4. The medical instrument assembly of claim 3, wherein the centerlines of the three peripheral coilpipes are disposed a substantially equal distance apart from each other.

5. The medical instrument assembly of claim 1, wherein the central and three peripheral coilpipes each have coil turns, and wherein longitudinally adjacent coil turns of each of the central and three peripheral coilpipes are spaced apart from each other.

6. The medical instrument assembly of claim 1, wherein the central coilpipe surrounds a central lumen, and also including a lengthwise translatable medical-end-effector activation cable disposed in the central lumen.

7. A medical instrument assembly comprising:
    a medical tubular assembly with at least four medical coilpipes together having a distal end portion insertable within a patient, wherein the medical coilpipes include a central coilpipe and at least three peripheral coilpipes disposed outward of the central coilpipe, wherein the at least four medical coilpipes are wound from a continuous length of wire, and wherein the three peripheral coilpipes each surround a separate peripheral lumen;
    a proximal medical instrument member connected to the medical tubular assembly;
    a distal medical instrument member connected to the distal end portion; and
    a separate and lengthwise translatable medical-instrument-member articulation cable disposed in each of the separate peripheral lumens, wherein the medical-instrument-member articulation cables are attached to the distal medical instrument member to articulate the distal medical instrument member with respect to the proximal medical instrument member.

8. The medical instrument assembly of claim 7, wherein the distal end portion is endoscopically insertable within a patient.

9. The medical instrument assembly of claim 8, wherein each of the central and at least three peripheral coilpipes has a centerline, and wherein the centerlines of the at least three peripheral coilpipes are disposed substantially equi-angularly apart from each other about the centerline of the central coilpipe.

10. The medical instrument assembly of claim 9, wherein the centerlines of the at least three peripheral coilpipes are disposed a substantially equal distance apart from each other.

11. The medical instrument assembly of claim 7, wherein the central and at least three peripheral coilpipes each have coil turns, and wherein longitudinally adjacent coil turns of each of the central and at least three peripheral coilpipes are spaced apart from each other.

12. The medical instrument assembly of claim 7, wherein the central coilpipe surrounds a lumen adapted to contain a lengthwise translatable medical-end-effector activation cable.

13. A medical instrument assembly comprising:
    a medical tubular assembly with four medical coilpipes together having a distal end portion insertable within a patient, wherein the four medical coilpipes include a central coilpipe and first, second, and third peripheral coilpipes disposed outward of the central coilpipe, wherein the four medical coilpipes consist essentially of a continuous length of monolithic wire, wherein one traveling along the wire would make a first loop once around a centerline of the first peripheral coilpipe, then would make a second loop once around a centerline of the second peripheral coilpipe, and then would make a third loop once around a centerline of the third peripheral coilpipe, wherein portions of the traveled wire not including the first, second and third loops would at least partially bound a centerline of the central coilpipe, and wherein the three peripheral coilpipes each surround a separate peripheral lumen;

a proximal medical instrument member connected to the medical tubular assembly;

a distal medical instrument member connected to the distal end portion; and a separate and lengthwise translatable medical-instrument-member articulation cable disposed in each of the separate peripheral lumens, wherein the medical-instrument-member articulation cables are attached to the distal medical instrument member to articulate the distal medical instrument member with respect to the proximal medical instrument member.

14. The medical instrument assembly of claim 13, wherein the wire is a superelastic wire.

15. The medical instrument assembly of claim 14, wherein the distal end portion is endoscopically insertable within a patient.

16. The medical instrument assembly of claim 13, wherein the centerlines of the first, second and third peripheral coilpipes are disposed substantially 120degrees apart from each other about the centerline of the central coilpipe, and wherein the centerlines of the first, second and third peripheral coilpipes are disposed a substantially equal distance apart from each other.

17. The medical instrument assembly of claim 13, wherein the central and the first, second and third peripheral coilpipes each have coil turns, and wherein longitudinally adjacent coil turns of each of the central and the first, second and third peripheral coilpipes are spaced apart from each other.

18. The medical instrument assembly of claim 13, wherein the central coilpipe surrounds a lumen adapted to contain a lengthwise translatable medical-end-effector activation cable.

* * * * *